US008998105B2

(12) United States Patent
Selby et al.

(10) Patent No.: US 8,998,105 B2
(45) Date of Patent: Apr. 7, 2015

(54) SPRAY GENERATOR

(75) Inventors: Robert Gordon Maurice Selby, Hertfordshire (GB); Martin Scott Goodchild, Cambridgeshire (GB)

(73) Assignee: The Technology Partnership Plc, Herts (GB)

( * ) Notice: Subject to any disclaimer, the term of this patent is extended or adjusted under 35 U.S.C. 154(b) by 1164 days.

(21) Appl. No.: 12/995,243

(22) PCT Filed: May 29, 2009

(86) PCT No.: PCT/GB2009/050594

§ 371 (c)(1), (2), (4) Date: Feb. 11, 2011

(87) PCT Pub. No.: WO2009/144510

PCT Pub. Date: Dec. 3, 2009

(65) Prior Publication Data

US 2011/0180622 A1 Jul. 28, 2011

(30) Foreign Application Priority Data

May 30, 2008 (GB) .................................. 0809876.6

(51) Int. Cl.

| | |
|---|---|
| ***B05B 1/08*** | (2006.01) |
| ***B05B 3/04*** | (2006.01) |
| ***A61M 11/06*** | (2006.01) |
| ***B05B 1/32*** | (2006.01) |
| ***B05B 1/30*** | (2006.01) |
| ***B05B 1/34*** | (2006.01) |
| ***B05B 17/00*** | (2006.01) |

(52) U.S. Cl.
CPC .................................. *B05B 17/0646* (2013.01)

(58) Field of Classification Search
USPC ............... 239/4, 102.1, 102.2, 338, 456, 459, 239/533.13, 533.14, 583, 576–579, 99, 239/533.15; 137/511, 522, 528, 535, 538, 137/540, 542, 543.15; 310/326, 327; 347/47
See application file for complete search history.

(56) References Cited

U.S. PATENT DOCUMENTS

| | | | | |
|---|---|---|---|---|
| 3,524,593 | A * | 8/1970 | Buckley et al. | 239/583 |
| 5,435,282 | A | 7/1995 | Haber et al. | |
| 5,685,485 | A | 11/1997 | Mock et al. | |
| 2004/0050953 | A1* | 3/2004 | Terada et al. | 239/102.2 |
| 2004/0164101 | A1 | 8/2004 | Cornet et al. | |
| 2004/0195394 | A1* | 10/2004 | Cornet et al. | 239/569 |
| 2005/0167519 | A1* | 8/2005 | Holm et al. | 239/4 |
| 2006/0289673 | A1* | 12/2006 | Wang et al. | 239/102.1 |
| 2007/0119968 | A1* | 5/2007 | Collins et al. | 239/102.1 |

FOREIGN PATENT DOCUMENTS

WO WO-95/25601 A1 9/1995

* cited by examiner

*Primary Examiner* — Melanie Tyson
*Assistant Examiner* — Thomas Berez
(74) *Attorney, Agent, or Firm* — Tarolli, Sundheim, Covell & Tummino LLP

(57) ABSTRACT

A spray generator (10) including: a membrane (40) having a perforate portion through which, in use, a fluid is caused to flow when the membrane (40) is vibrated; an electronically-driven or a piezoelectrically driven actuator for vibrating the membrane (40); a chamber (18) for storing fluid for supply to a surface of the membrane (40); and a sealing element (13) located in and movable within the chamber (18) between a first position in which fluid flow from the chamber (18) through the membrane (40) is prevented and a second position in which fluid flow from the chamber (18) through the membrane (40) is allowed.

13 Claims, 6 Drawing Sheets

SPRAY GENERATOR

FIELD OF THE INVENTION

This invention relates to a spray generator and, in particular, a spray generator having an electronically driven or piezoelectrically driven actuator for vibrating a perforate membrane, typically for use in electronic aerosols and the like.

BACKGROUND OF THE INVENTION

When piezoelectrically actuated aerosols are used in fast-moving consumer goods such as household and personal care products, they are often required to prevent fluid leakage from the device when it is not in use. Such applications could include, but are not limited to, fragrance dispensers, cosmetic products and household cleaning products.

In these types of applications, it is often the case that the droplets which are generated need to be sufficiently large that they will land on a surface, rather than simply evaporate into the atmosphere once they have been dispensed. Typically, these droplets will have an average droplet diameter in the region of 20 to 60 microns and a spray generator that is capable of producing such droplets will typically have nozzle diameters in the region of 10 to 20 microns. In some of the applications referred to above, the fluid to be dispensed has a relatively low surface tension and a relatively low viscosity and, as a result, fluid can easily flow through the nozzles of a membrane when the device is not in use. This fluid flow is driven by a combination of capillary action and pressure differences. This pressure difference comes from the fluid head behind the membrane and, if the chamber containing the fluid cannot maintain equilibrium with the atmosphere, differences caused by changes in atmospheric temperature or pressure.

One method of preventing fluid flow through those nozzles when the device is not in use is to apply a negative pressure to the fluid in the region directly behind the perforate membrane. However, maintaining a negative pressure behind the membrane of such a device within a sealed chamber, consisting of a fluid feed and a fluid reservoir, is not a trivial task. In particular, any mechanism for supplying a negative pressure will need to cope with pressure changes resulting from changes in ambient pressure or temperature.

Thus, an alternative method of preventing unwanted fluid flow through a perforate membrane is required.

SUMMARY OF THE INVENTION

According to the present invention, there is provided a spray generator comprising:

a membrane having a perforate portion through which, in use, a fluid is caused to flow when the membrane is vibrated;

an electronically driven or a piezoelectrically driven actuator for vibrating the membrane;

a chamber for storing fluid for supply to a surface of the membrane; and a sealing element located in and moveable within the chamber between a first position in which fluid flow from the chamber to the membrane is prevented and a second position in which fluid flow from the chamber to the membrane is allowed.

Thus, the present invention provides a movable sealing element which, in certain embodiments, is preferably compliant, such that it can be moved into direct physical contact with the perforate membrane. By creating a seal around any perforations in the membrane, unwanted fluid flow can be prevented whilst the device is not in use.

Preferably, in the present invention the movable sealing element moves principally perpendicular to the membrane (or other sealing) surface. This minimises the required travel of the seal and any biasing force when closed assists in the sealing of the surface. Further, the present invention preferably utilises any pressure difference across the membrane to push the compliant seal against the membrane and improve sealing. This is accomplished by designing the seal such that its back surface is primarily exposed to the pressure that the fluid is under. As its front surface is exposed to atmospheric pressure when sealed this adds a beneficial biasing force. This beneficial force is not present when the back of the seal is not subjected to the same pressure as the fluid. If the seal was on the other side of the membrane this biasing force would be detrimental to sealing rather than beneficial.

A further benefit of this design is that the sealing element can be thin and compliant in nature as it does not have to resist bending in order to maintain a complete seal. In a preferential embodiment, the sealing element is, when sealed, unconstrained from moving tangentially relative to the membrane and, when subjected to a typical pressure difference, deforms to seal against the membrane.

For the seal to perform it will need to be sealed for pressure differences as low as 1 kPa. For this to occur it needs to both deform to the surface it is sealing against and be compliant enough to seal against surfaces which are not ideally smooth (i.e. have surface roughness). To achieve compliance, the Durometer (Shore A) hardness should be of value 70 or lower and more ideally of value 50 or lower. The seal will ideally deform up to 0.1 mm, more ideally up to 1.0 mm under such pressures to ensure good seal contact. Modelling the seal section in contact with the membrane as a simply supported flat plate under large deflection the following formula approximately relates the pressure difference, q, to the deflection of the seal at its centre, y:

$$\frac{qa^4}{Et^4} \approx 1.451\frac{y}{t} + 0.376\left(\frac{y}{t}\right)^3$$

where E is the Young's Modulus of the material, t is its thickness and Poisson's ratio has been taken to equal 0.3. 'a' is the seal outer radius and depending on spray generator design will typically vary between 2 mm and 6 mm. For a 0.5 mm thick seal the Young's Modulus should ideally be less than or equal to $\sim 10^8$ or more ideally less than or equal to $\sim 10^6$. Whilst reducing thickness further allows for increased Young's Modulus, the seal becomes more fragile.

Preferably, the present invention further includes an actuating device for moving the sealing element between its two positions. The sealing element may be mounted on the actuating device. The actuating device may be a plunger which is movable towards and away from the perforate membrane. The actuator may pass through a wall of the chamber and, if this is this case, a seal is preferably provided around the actuating device to prevent fluid flow from the chamber passed the seal.

The sealing element preferably forms part of a sealing device having a mounted outer portion, wherein the sealing element is connected to and movable relative to the outer portion. The outer portion of the sealing device may be mounted in or on the chamber. The actuator and the membrane may be mounted in the outer portion of the sealing device. The outer portion of the sealing device may be mounted within an outer wall of the chamber.

In an alternative construction, the sealing device may extend through, in at least two locations, a wall defining the chamber such that movement of portions of the sealing device external to the chamber causes movement of the sealing element between the first and second positions.

The sealing device may be integrally formed with the walls of the chamber in such a way that a pivoting movement of the sealing device relative to the chamber walls can be achieved. The integral connection between the wall of the chamber and the sealing device may be relatively thin compared to the thickness of the wall to enable movement of the sealing device.

The sealing element may be mounted on or be connected to a shape memory alloy (SMA) which, upon activation, causes movement of the sealing element relative to the perforate membrane. Alternatively, the sealing element may be mounted on an arm which passes through a wall of the chamber and has a deformable seal preventing fluid flow between the wall and the arm.

Where shape memory alloy is provided to cause movement of the sealing element, it is preferable that activation of the shape memory alloy causes movement of the sealing element away from the membrane, with the deactivation of the shape of any alloy causing movement in the opposite direction and into sealing engagement with the perforate membrane.

Biasing means may be provided for urging the sealing element to the desired at rest position, which is preferably in sealing engagement with the perforate membrane.

The sealing device may include one or more openings located between the sealing element and the chamber such that fluid can pass through the sealing device within the chamber. The openings may be provided between a plurality of spokes in the sealing device.

The sealing element may have a flat sealing face for sealing the perforate portion of the membrane from the rest of the chamber. The flat sealing face is preferably in direct contact with the perforate portion of the membrane when the sealing element is in the first position.

The sealing face may, alternatively, include a circumferential bead for contacting the perforate membrane around the perforate portion, so as to prevent fluid flow through the perforate portion.

A fluid supply means is preferably provided to allow fluid to enter the chamber to replace that which is dispensed through the perforate membrane in use.

The fluid supply means is preferably on the opposite side of the sealing device to the perforate membrane such that fluid can flow through the openings in the seal device in order to reach the perforate membrane. A spacer may be provided on the chamber side on the perforate membrane, the spacer having an opening to permit fluid from the chamber to reach the perforate membrane wherein the sealing element in the first position is arranged to block the opening in the spacer. The sealing element may extend into the opening and the spacer when the sealing element is in the first position so as to prevent fluid flow from the chamber to the membrane.

BRIEF DESCRIPTION OF THE DRAWINGS

Examples of the present invention will now be described with reference to the accompanying drawings, in which.

DETAILED DESCRIPTION OF THE INVENTION

Figure 1:
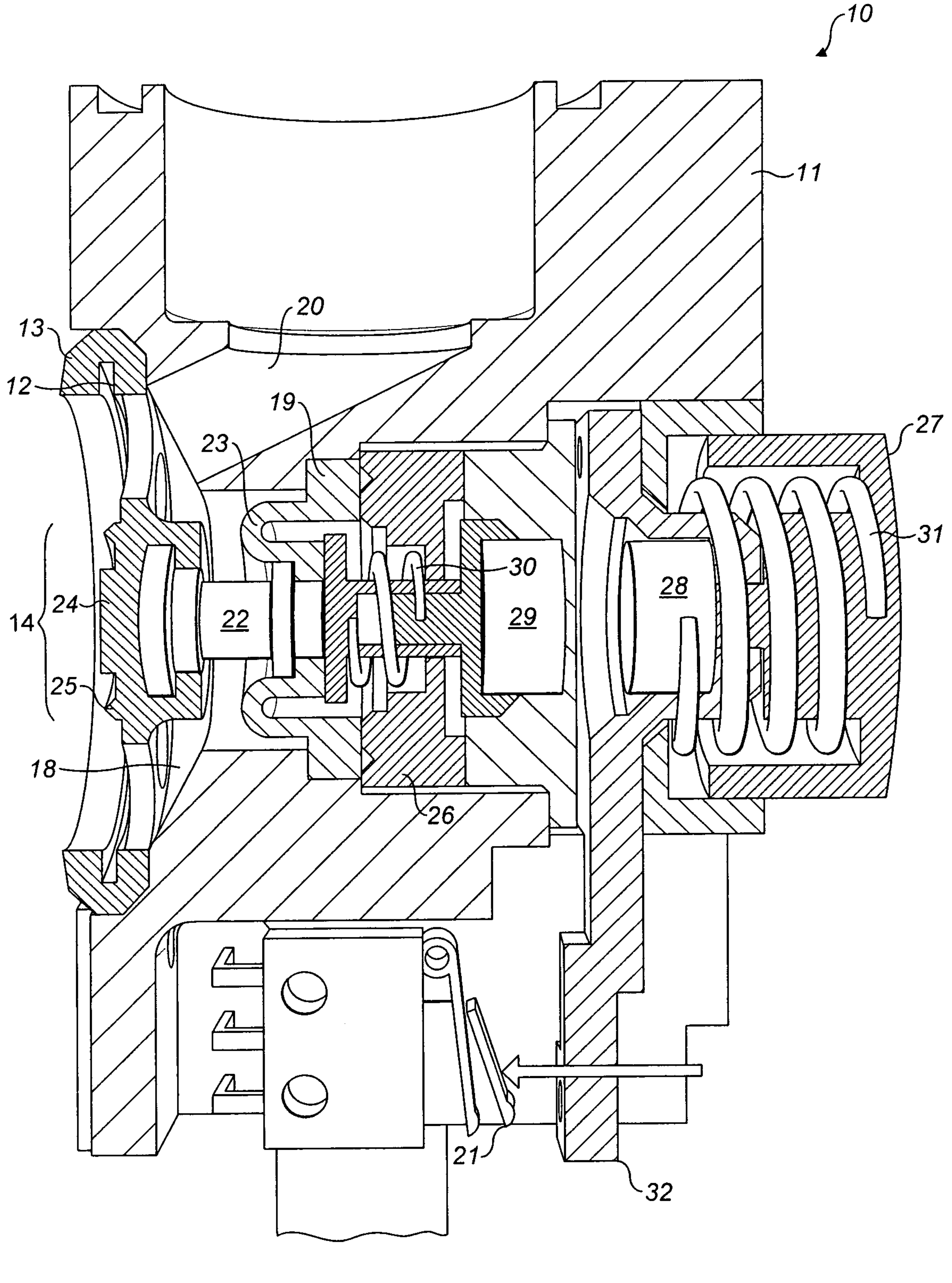
FIG. 1 shows a first example of a spray generator according to the present invention.

FIG. 1 shows a first example of a spray generator 10 which is formed in a main body 11. Although not shown in FIG. 1, a perforate membrane would, in use, be located in slot 12 within sealing element 13, with the perforate portion of the membrane being located substantially at the centre of the membrane such that it aligns with the sealing portion 14 at the centre of element 13.

Figure 2A:
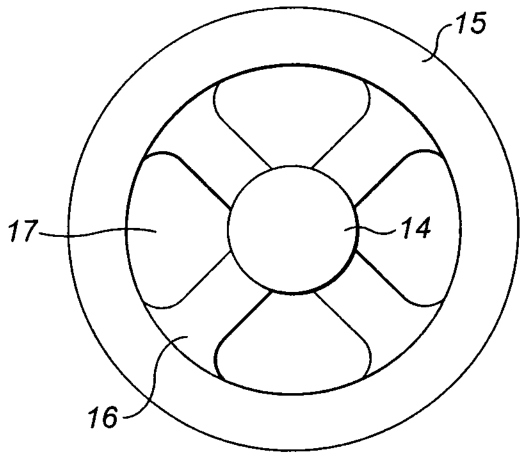
FIG. 2 shows one possible design of a spoked sealing device.

The sealing element 13 is shown in greater detail in FIG. 2*a* in which the outer substantially annular section can be seen and it is this outer section which supports the perforate membrane in slot 12. The central sealing portion 14 can also be seen and it is supported, spaced from the outer portion 15, by plurality of spokes 16. Thus, a plurality of openings 17 are provided between adjacent spokes and the outer annular portion 15. When the perforate membrane is in place as shown in FIG. 2*a, b* chamber 18 is defined by the perforate membrane, walls of the main body 11 and a rolling seal 19. The sealing element and, in particular, the central portion 14 of the sealing element is movable within the chamber 18. A fluid inlet 20, typically from a bulk reservoir (not shown) is provided into chamber 18 and is located on the opposite side of the sealing element to the perforate membrane. Thus, the fluid flow is able to pass through the opening 17 in the sealing element in order to reach the perforate membrane for dispensing.

The rolling sealing 19 is connected between the main body 11 and a plunger portion 22 which is, in turn, connected to the central portion 14 of the sealing element 13. Movement of the plunger towards and away from the perforate membrane causes flow to be either prevented or permitted through the perforate membrane. The rolling seal 19 has a rolling section 23 which moves with the plunger thereby allowing the plunger to move within the chamber, but the seal maintains the fluid integrity of that chamber.

The central portion of the sealing element has a substantially flat sealing face 24 which contacts the perforate membrane over the region of the perforations, such that no fluid flow is permitted through those perforations. Alternatively and/or additionally, a circumferential bead 25 may be provided on the central portion 14 of the sealing element such that this surrounds the region of the perforate membrane having perforations in order to prevent fluid flow from the chamber 18 through those perforations.

The sealing element is preferably formed from some compliant material or at least the flat sealing face 24 and/or the circumferential bead 25 are formed from compliant material in order to provide a better seal with the perforate membrane. In order for the central portion 14 of the sealing element 13 to move relative to the perforate membrane, other portions, such as the spokes, of the sealing element 13 must be flexible.

The rolling seal 19 is held in place by means of a clamp block 26. An activation button 27, biased to an outward position (the right in FIG. 1), is connected to a magnet which, in the at rest position is spaced from a secondary magnet 29 such that the magnets are not attracted to each other. By pressing the activation button 27 such that magnet 28 moves closer to magnet 29, the two magnets are caused to attract one another such that magnet 29 is caused to move towards magnet 28. Magnet 29 is, although not shown in FIG. 1, connected to the plunger 22 thereby causing the central portion 14 of the sealing element to be moved away from the perforate membrane. This enables fluid to flow through the perforate membrane once it has been actuated. Biasing means 30 and 31 are provided to separate the magnets 28, 29. Biasing means 30 returns the central portion 14 of the sealing element 13 into contact with the perforate membrane, once the activation button 27 has been released by a user. Biasing means 31 is sufficiently strong to overcome the attraction of the magnets and will separate them once a user has released button 27.

When the actuation button 27 is pressed, and activation arm 32 is brought into contact with a switch 21 which activates an actuator for causing the perforate membrane to vibrate. This actuator is typically a piezoelectric actuator or some other electronically driven actuator and can be seen in FIG. 3.

Figure 2B:
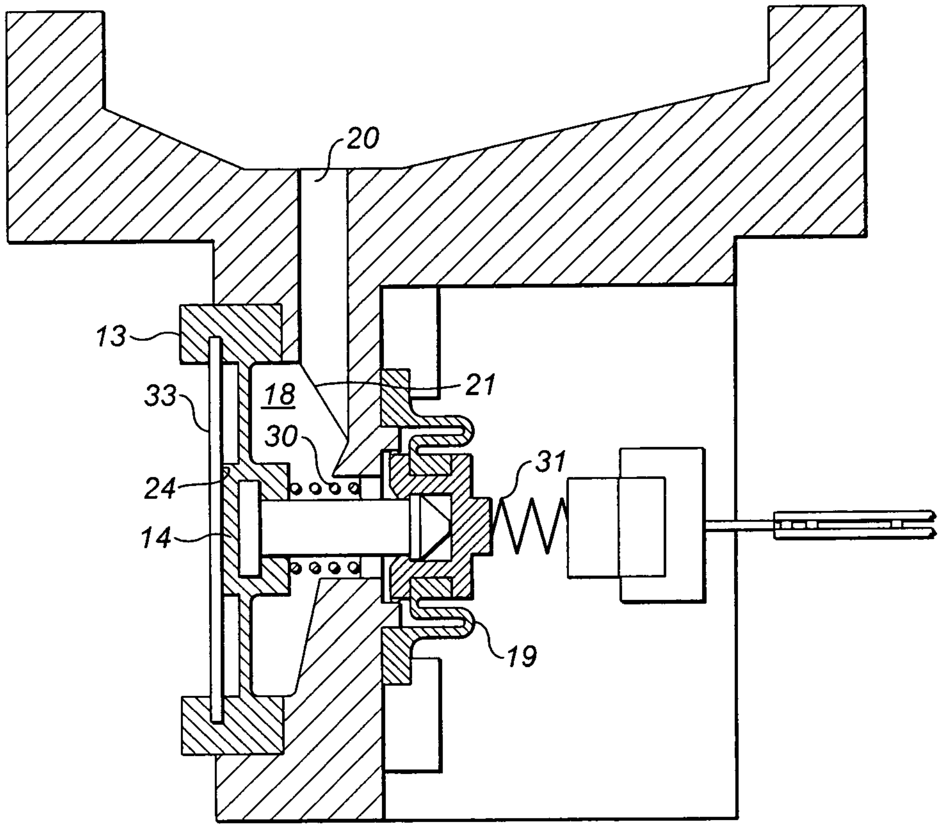

A simplified schematic of a slightly different design is shown in FIG. 2*b*, but like reference numerals have been included. FIG. 2*b* does show the provision of and location of a perforate membrane 33 and the central portion 14 of the sealing element 13 can be seen in an at rest position in which the sealing face 24 is in contact with the perforate membrane 33.

In the example in FIG. 2*b*, biasing means 30, typically taking the form of a spring, is located within chamber 18, whereas in FIG. 1 it is external to the chamber. The location of the biasing means is not important.

Further simplified mechanisms for causing a sealing element to be moved into and out of engagement with a perforate membrane are shown in the following figures. In the following figures, the perforate membrane is shown having a domed perforate portion, whereas in FIG. 2*b*, the perforate membrane is substantially planar. The exact form of the perforate membrane is not important, but it is important that the sealing face of the sealing element prevents fluid flow through the perforations of the perforate element. Thus, it is preferable for the sealing face to conform to the shape of the perforate portion of the perforate membrane as this will minimise or preclude there being any small retained volume which can then leak from the perforate membrane, but, as described above, the seal may simply be made by way of a circumferential bead extending around the perforate portion of the membrane.

Figure 3A:
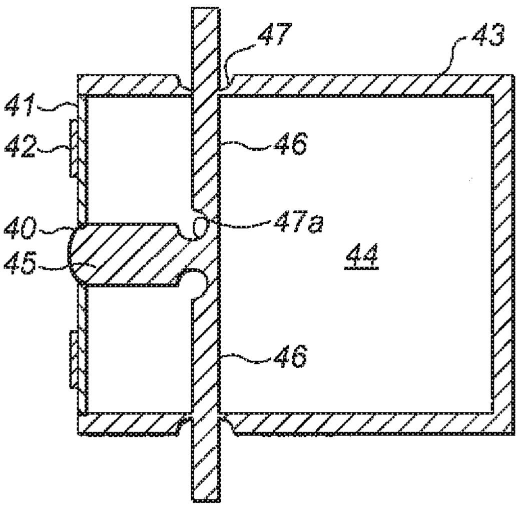
FIG. 3 shows a further example of a spray generator.
Figure 3B:
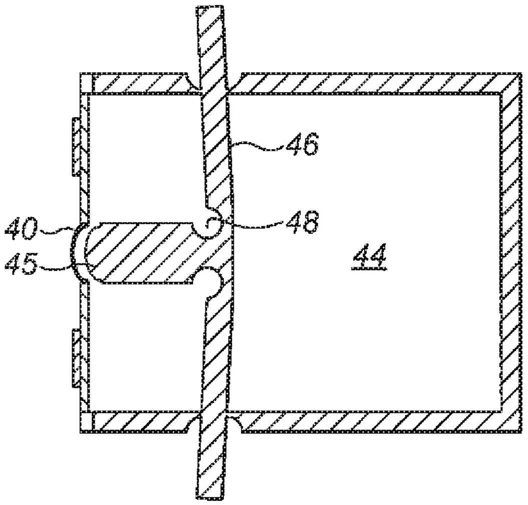

Turning now specifically to FIGS. 3*a* and 3*b*, a perforate membrane 40 is mounted in a substrate 41 and, on substrate 41, a piezoelectric element 42 taking the form of an annulus is provided. Actuation of the piezoelectric annulus causes the substrate and subsequently the membrane to vibrate causing fluid to pass through the perforate membrane. The actuator in its broadest sense takes the form of a composite thin walled structure which is arranged to operate in a bending mode.

The perforate membrane and substrate are mounted to the walls 43 of a chamber 44 and a sealing element having a central, membrane sealing portion 45 is provided within chamber 44. In this example, the sealing element also includes a pair of arms 46 that extend away from the central portion 45 to locations external to the chamber 44. In this example, the arms are formed integrally with the walls 43 of the chamber and, as such, no additional sealing is required at the point at which the arms 46 pass through the walls 43. However, the arms may simply pass through holes in the chamber wall 43, as long as appropriate seals are provided to prevent fluid exiting the chamber at those points.

The connection 47 of the arms 46 with the walls 43 is by way of a relatively thin section of wall 43, such that, as can be seen in FIG. 3*b*, the arms can be flexed at the joint, like a hinge, so as to cause the central membrane sealing element 45 to be moved away from the perforate membrane 40 in order to permit fluid flow from the chamber 44 out through the perforate membrane. In addition, the connection 47*a* between the arms 46 and the central portion 45 is notched so as to form a hinge portion 48. The seal mechanism shown in these figures also clearly highlights another benefit of this invention, the fact that any pressure difference across the membrane creates a beneficial biasing force that assists in sealing.

Figure 4A:
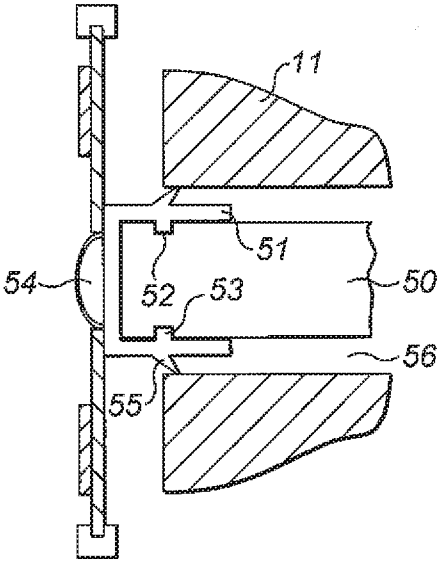
FIG. 4 shows a yet further embodiment of a spray generator.
Figure 4B:
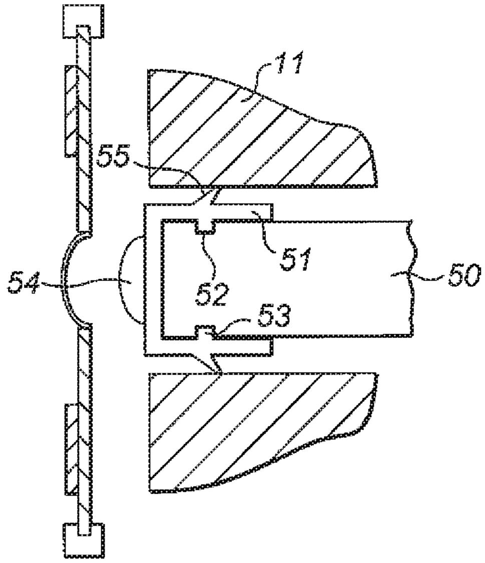

FIGS. 4*a* and 4*b* show an alternate embodiment in which the seal with the perforate membrane 40 is provided by way of a plunger 50 on which an integrated membrane seal and sliding seal element 51 is mounted by way of a notch 52 in the plunger 50 and a corresponding projection 53 on the inner portion of the seal 51. The seal 51 is provided with a membrane sealing portion 54 and a sliding seal 55 such that the plunger is movable within channel 56 defined within the main body 11. The remainder of main body 11 is not shown, but, as with other examples, a chamber into which fluid can be supplied to an inlet is provided and is defined, typically by the main body 11 and the perforate membrane and substrate. FIG. 4*b* shows the plunger in a position in which it has been moved away from the perforate membrane in order to permit fluid to be dispensed. In this case, the sliding seal 55 has simply slid along the inner wall of the channel 56, thereby maintaining the fluid tight seal to prevent fluid exiting the chamber past the plunger 50.

Figure 5A:
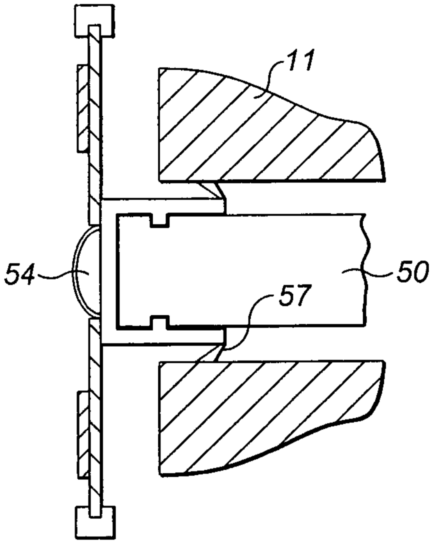
FIG. 5 shows another embodiment of a spray generator.
Figure 5B:
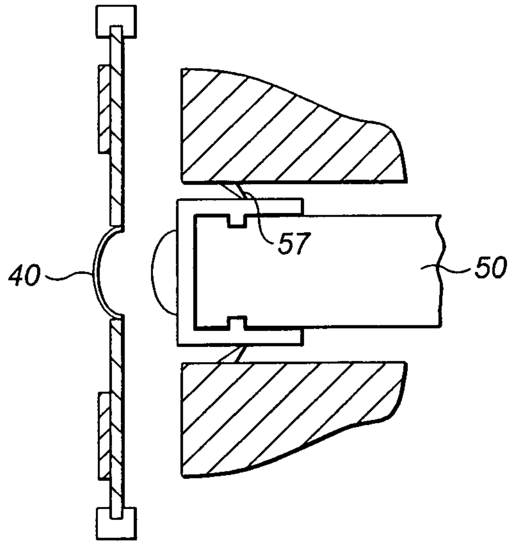

FIGS. 5*a* and 5*b* show a similar embodiment to those of FIG. 4, but in which, rather than mounting a sliding seal 55 on the membrane sealing element connected to the plunger 50, a sliding seal 57 is mounted to the wall of the chamber. Thus, as can be seen in FIG. 5*a*, when the plunger is in the at rest position with the membrane sealed, the sliding seal 57 mounted on the wall of channel 56 is in contact with the sealing element mounted on the end of plunger 50. As the plunger is withdrawn as shown in FIG. 5*b*, the sliding seal 57 runs along the outer portion of the seal mounted on the end of plunger 50 thereby maintaining the fluid tight integrity.

Figure 6A:
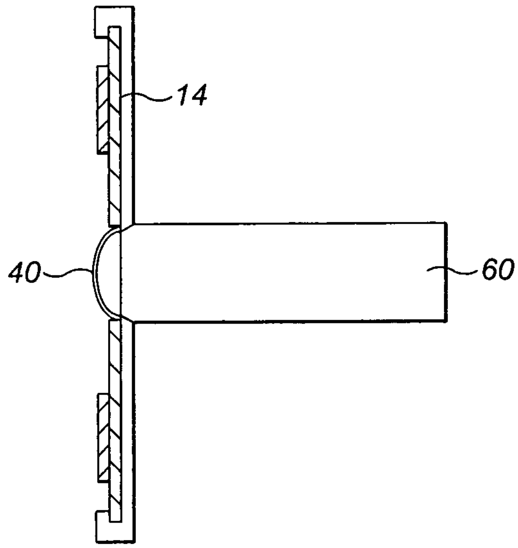
FIG. 6 shows a yet further still embodiment of a spray generator.
Figure 6B:
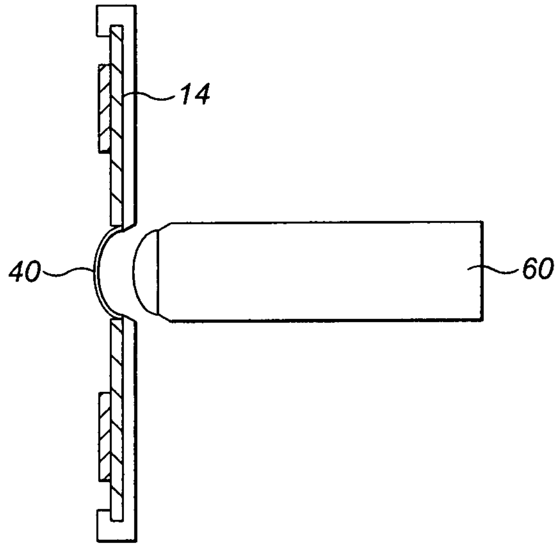

In FIGS. 6*a* and 6*b*, a rigid membrane seal plunger 60 is provided and this is movable into and out of engagement with the perforate membrane 40. The seal plunger 60 does not include a seal (as in FIG. 4, item 51) and is a metal or plastic part shaped to fit the profile of the membrane 40 and provides a membrane seal with the membrane sealing element 14. The membrane sealing element 14 is integrated with the head-mount seal to make a single component that can be easily assembled with the spray head.

The motion of the seal plunger could be could be constrained by a sliding seal (57) mounted on the wall of the channel 56 as shown in FIGS. 5*a* and 5*b*, or by other means, as shown in FIG. 10.

Figure 7A:
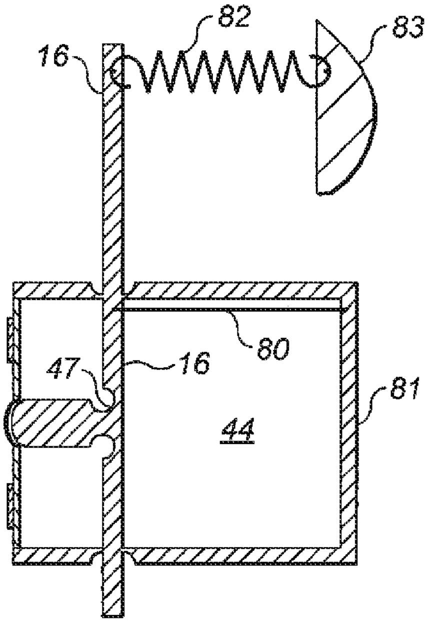
FIG. 7 shows the provision of an internal SMA actuator.
Figure 7B:
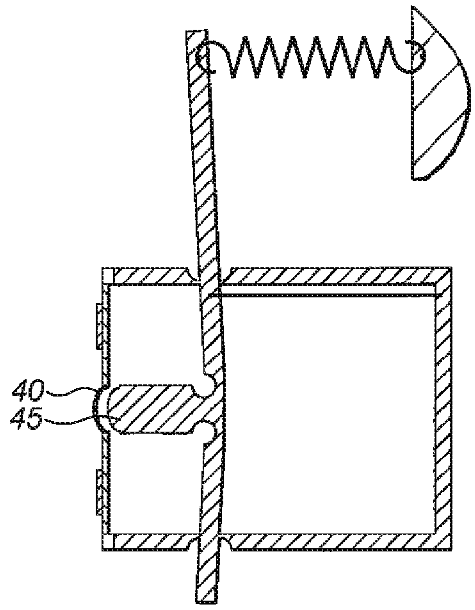

FIG. 7 shows one method of actuating the plunger shown in FIGS. 3*a* and 3*b*. In this example, a shape memory alloy actuator 80 is mounted within the chamber 44 and is connected to an end wall 81 and to at least one of the arms 16. An external portion of one of the arms 16 is connected to a biasing means, in the form of a spring 82, which is, at its other end, connected to a mounting surface 83. Thus, upon actuation of the shape memory alloy, the shape memory alloy 80 contracts, thereby drawing the membrane sealing element 45 away from the perforate membrane 40, as shown in FIG. 6*b*. This contraction of the shape memory alloy 80 causes spring

82 to extend and apply a restoring force to arm 16 which, upon de-activation of the shape memory alloy, causes the membrane sealing element 45 to return to a position in which it seals against perforate membrane 40.

Figure 8A:
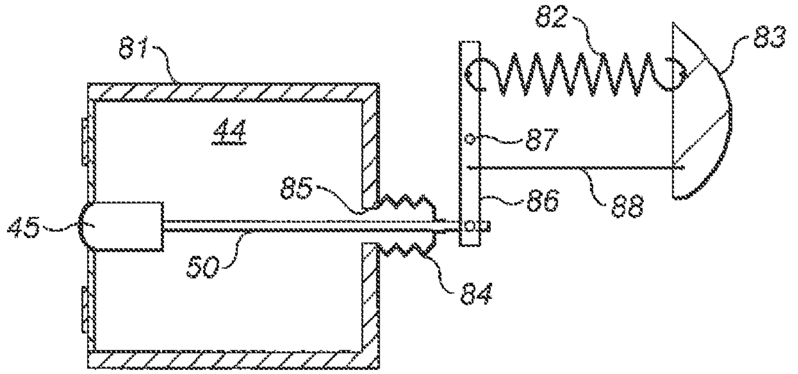
FIG. 8 shows the provision of an external SMA actuator.
Figure 8B:
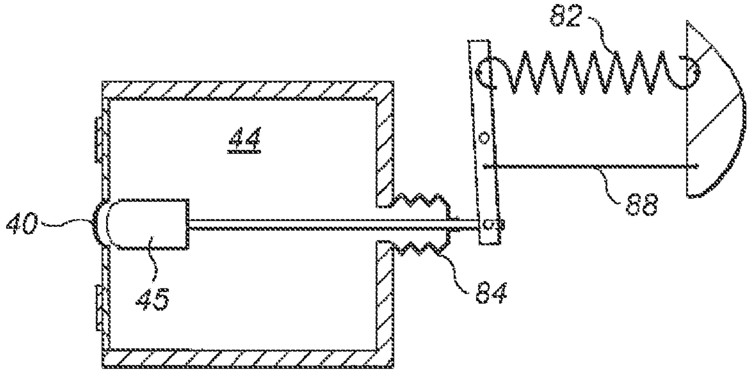

An alternative actuation method is shown in FIGS. 8*a* and 8*b* in which the membrane sealing element 45 is mounted to a plunger 50 which extends through end wall 81 of the chamber 44, a bellows type seal 84 or a rolling seal is provided between plunger 50 and the opening 85 and the end wall 81 of the chamber. The plunger is then connected to a lever arm 86 which can pivot about pivot 87. A shape memory alloy 88 is connected between a rigid surface and the lever 86 and, on the opposite side of the pivot 87, a return spring 82 is also connected between the lever and the rigid mounting point 83. Thus, as with the example in FIG. 7, actuation of the SMA causes it to contract, drawing the plunger away from the membrane, thereby permitting flow to exit through perforate membrane 40. When the SMA is de-activated, the return spring 82 causes the lever to pivot back to the at rest position causing the plunger to be moved into the chamber 44 and for the sealing element to contact the perforate membrane again.

Figure 9A:
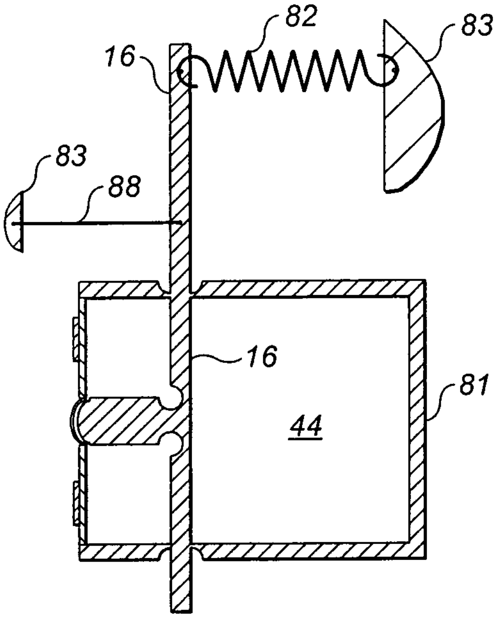
FIG. 9 shows a further construction using an external SMA actuator.
Figure 9B:
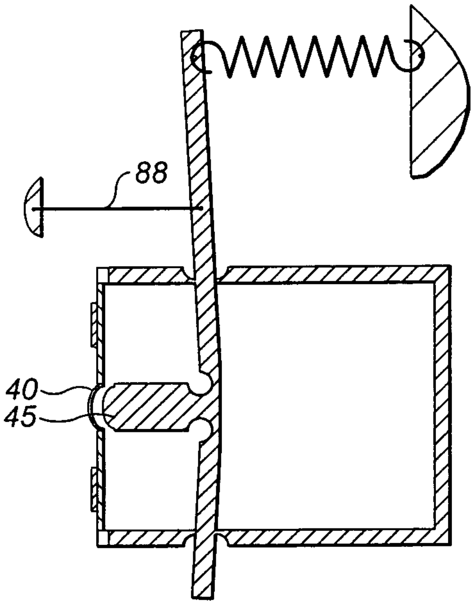

In FIG. 9, a further construction using an external SMA actuator is shown and in this example the SMA actuator 88 is positioned such that, when un-activated, the spring 82 causes the arm 16 to be in a position in which the sealing element 45 is in contact with the perforate membrane 40, but upon activation and therefore contraction of the shape memory alloy 88, the arm 16 is caused to deflect against the biasing force of spring 82 and cause the membrane sealing element 45 to be moved away from the perforate membrane 40. Upon deactivation of the SMA, the return spring then causes the seal to be reformed.

Figure 10A:
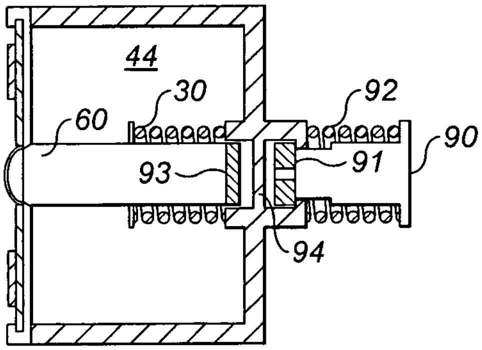
FIG. 10 shows an actuator method using external magnetic actuation.
Figure 10B:
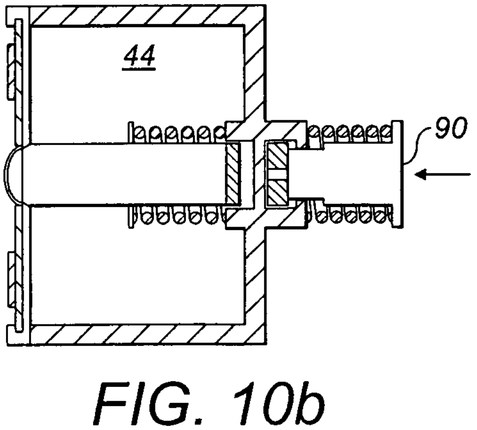
Figure 10C:
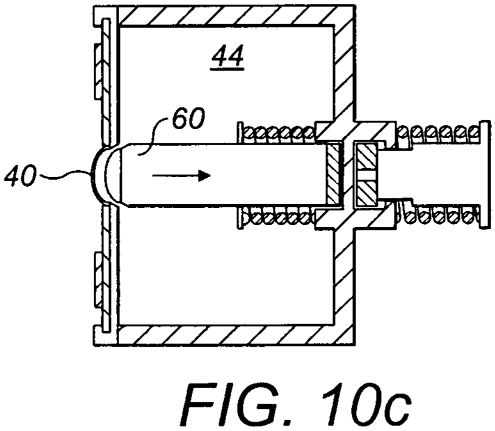

FIGS. 10*a* to 10*c* illustrate a further actuation method similar to that shown in FIG. 1 in which an external activation button 90 is connected a magnet 91 and is biased outwardly by spring 92. The sealing element 60, similar to that shown in FIG. 6, is biased into contact with the perforate membrane 40 by way of a spring 30. A further magnet 93 is provided on the end opposite to the membrane seal and, in the at rest position, magnets 92 and 93 are separated by sufficient distance that they do not attract one another. However, upon activation of button 90, magnet 91 is brought sufficiently close to magnet 93 that they are attracted and, as magnet 91 is prevented from further movement by way of locking element 94, magnet 93 is drawn towards magnet 91. This therefore causes the plunger on which the sealing element is mounted to move away from the perforate membrane in order to permit flow through the perforate membrane 40.

The invention claimed is:

1. A spray generator comprising:

a membrane having a perforate portion through which, in use, a fluid is caused to flow when the membrane is vibrated;

an electronically-driven or a piezoelectrically driven actuator for vibrating the membrane;

a chamber for storing fluid for supply to a surface of the membrane;

a sealing element located in and movable within the chamber between a first position in which the sealing element contacts the membrane or actuator to prevent fluid flow from the chamber through the membrane and a second position in which fluid flow from the chamber through the membrane is allowed; and wherein the area of the back of the sealing element that is subjected to a chamber pressure is greater than the area of the front of the sealing element that is subjected to the chamber pressure when the sealing element is in the first position.

2. A spray generator according to claim 1, wherein the sealing element seals against the chamber side of the membrane or a substrate, the substrate being part of the actuator.

3. A spray generator according to claim 2, wherein the sealing element has a flat sealing face for sealing the perforate portion of the membrane from a portion of the chamber not sealed by the perforate portion, wherein the flat sealing face is in direct contact with the perforate portion of the membrane when the sealing element is in the first position.

4. A spray generator according to claim 1, wherein the sealing element includes a sealing face having a circumferential bead for contacting the perforate membrane or a substrate, the substrate being part of the actuator, around the perforate portion, so as to prevent fluid flow to the perforate portion.

5. A spray generator according to claim 1, wherein the actuator comprises a composite thin walled structure arranged to operate in a bending mode.

6. A spray generator according to claim 1, wherein the sealing element forms part of a sealing device having a mounted outer portion, wherein the sealing element is connected to and movable relative to the outer portion.

7. A spray generator according to claim 6, wherein the actuator and the membrane are mounted in the outer portion of the sealing device.

8. A spray generator according to claim 1, wherein the sealing element motion is principally perpendicular to the membrane surface.

9. A spray generator according to claim 1, wherein the sealing surface of the sealing element has a Durometer (Shore A) hardness of 70 or less.

10. A spray generator according to claim 1, wherein the material of the sealing element has a Young's Modulus of $10^8$ or less.

11. A spray generator according to claim 6, wherein the sealing device includes one or more openings located between the sealing element and the chamber such that fluid can pass through the sealing device within the chamber.

12. A spray generator according to claim 1, further comprising biasing means for urging the sealing element to the first position and an actuating device for moving the sealing element to the second position.

13. A spray generator according to claim 1, further comprising a biasing element for urging the sealing element to the first position and an actuating device for moving the sealing element to the second position.

* * * * *